United States Patent [19]

Sheridan John J.

[11] Patent Number: 5,044,951
[45] Date of Patent: Sep. 3, 1991

[54] DENTAL SPACE AND PERIODONTAL CAVITY MEASURING INSTRUMENT

[76] Inventor: Sheridan John J., 1401 Lake St. Unit E-9, Metairie, La. 70005

[21] Appl. No.: 514,149

[22] Filed: Apr. 25, 1990

Related U.S. Application Data

[63] Continuation-in-part of Ser. No. 358,597, May 30, 1989, Pat. No. 4,959,014.

[51] Int. Cl.$^5$ .............................................. A61C 19/04
[52] U.S. Cl. ........................................ 433/72; 33/514
[58] Field of Search ............... 433/72, 2, 3, 141, 147, 433/75, 215; 33/514, 531, 542, 513, 662, 514.1

[56] References Cited

U.S. PATENT DOCUMENTS

| | | | |
|---|---|---|---|
| 4,364,730 | 12/1982 | Axelsson | 433/72 |
| 4,552,531 | 11/1985 | Martin | 433/141 |
| 4,768,952 | 9/1988 | Loewenthal | 433/72 |
| 4,959,014 | 9/1990 | Sheridan | 433/72 |

*Primary Examiner*—Cary E. Stone
*Attorney, Agent, or Firm*—John M. Harrison

[57] ABSTRACT

A dental space and periodontal cavity measuring instrument for insertion in interdental or interproximal spaces between teeth and in periodontal cavities in both the upper and lower dental arches to determine the width of such spaces and the depth of the cavities, respectively, for appropriate treatment. The dental space and periodontal cavity measuring instrument is characterized by a centrally located handle provided with a pair of oppositely-extending single tips or multiple, elongated, graduated cylinders which terminate in graduated ends, for insertion in the interdental spaces and periodontal cavities. The calibrated cylinders and graduated ends may be extended in a straight line from the handle, or one or more cylinders in one or both of the calibrated and graduated tips may be angulated and the diameter of each cylinder may be indicated on the handle for size-identification purposes. The ends of the cylinder or stem tips may also be "waffled" with striations for ligature tucking purposes.

16 Claims, 1 Drawing Sheet

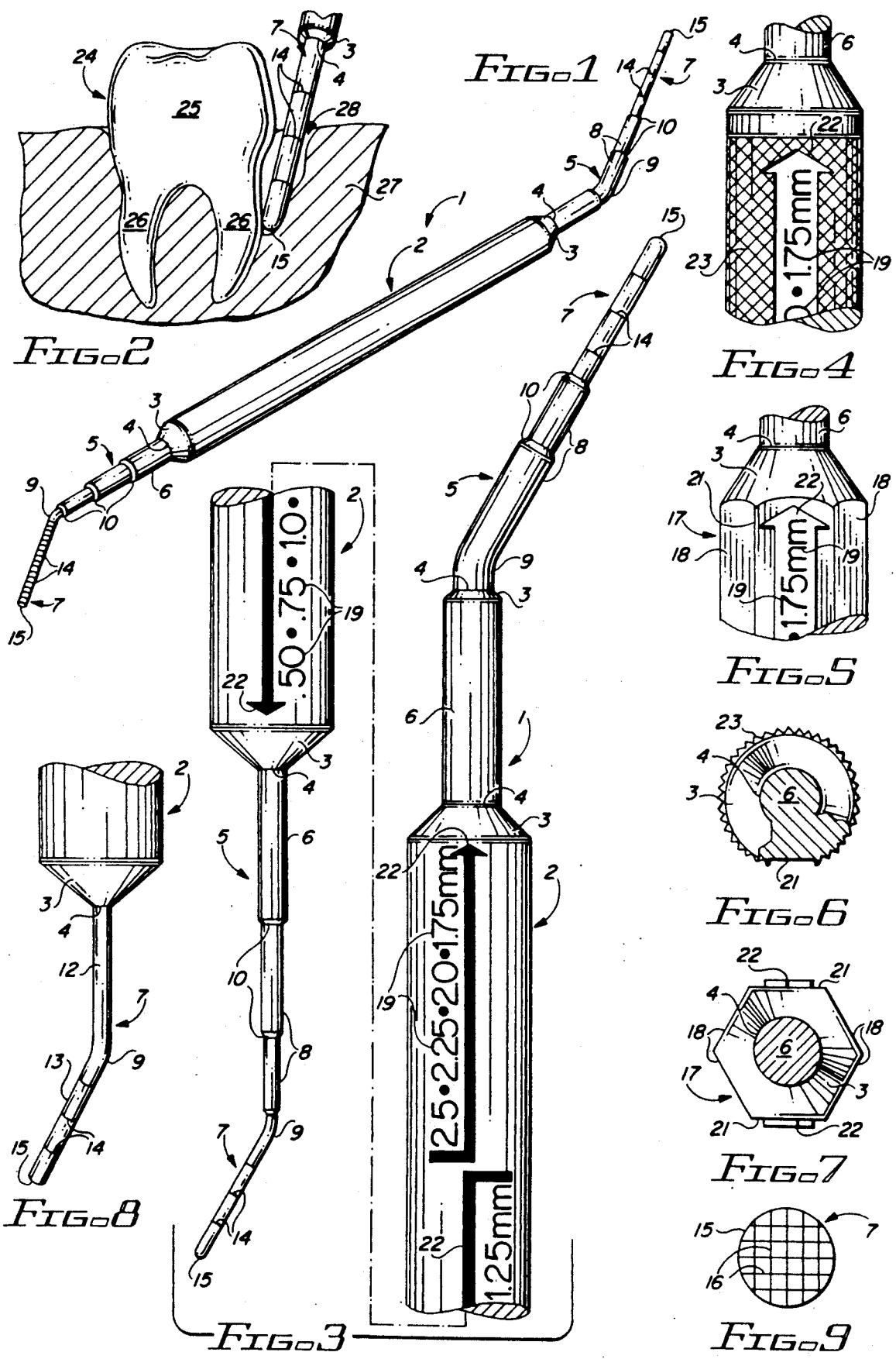

DENTAL SPACE AND PERIODONTAL CAVITY MEASURING INSTRUMENT

CROSS-REFERENCE TO RELATED APPLICATIONS

This application is a continuation-in-part of my copending U.S. patent application Ser. No. 07/358,597, filed May 30, 1989 now U.S. Pat. No. 4,959,014.

BACKGROUND OF THE INVENTION

FIELD OF THE INVENTION

This invention relates to orthodontic and periodontal instruments and more particularly, to a dental space and periodontal cavity measuring instrument which is designed for measuring naturally-occurring or mechanically-created interdental or interproximal spaces between teeth, as well as periodontal cavities in the bone adjacent to the teeth, to facilitate accurate orthodontic and periodontic treatment of the teeth. In a preferred embodiment of the invention the dental space and periodontal cavity measuring instrument is characterized by a handle having elongated calibrated and graduated cylinders extending from the ends thereof, and terminating in a graduated end portion. The cylinders are characterized in a preferred embodiment by multiple, graduated cylinders of selected diameter, length and number for accurate measurement of the interdental spaces and an end portion having marks or graduations for measuring the periodontal cavities. Alternatively, a single cylinder or stem or a pair of cylinders, each having a selected diameter, length and shape, may extend from a common handle for effecting the desired orthodontic and/or periodontic measurement. In a most preferred embodiment, at least one of the calibrated and graduated cylinders is angulated to facilitate convenient access to interdental spaces between the molars and bicuspids, between the bicuspids themselves, between the bicuspids and the adjacent cuspid teeth, and anterior incisor teeth and between the bone and gum structure and the tooth or teeth. Numerical indicia which indicates the diameter of each discrete cylinder in the calibrated and graduated cylinder tips is provided on the handle and the handle may be round or shaped in the configuration of a polygon, such as a hexagon, in non-exclusive particular. Furthermore, the end portions of the elongated tips may be provided with one or more slots or striations for engaging a ligature and tucking the end of the ligature in orthodontic practice.

One of the problems which exists in the practice of orthodontics and periodontics is that of accurately measuring interdental or interproximal spaces, or the spaces between adjacent teeth in the dental arches, as well as periodontal cavities which develop between the teeth and bone structure, in order to correct the defects by well known orthodontic and periodontic procedures, respectively. Accurate measurement of these interdental spaces and periodontal cavities is difficult, particularly when the spaces and cavities are located between and adjacent to the molars and the bicuspids, the bicuspids themselves or between the bicuspids and the cuspids, located at the back of, and centrally of the oral cavity, respectively. It is frequently necessary to determine this spacing and the depth of these cavities, not only for restoration and cosmetic purposes, but also to prevent foodstuff from wedging between the teeth and between the teeth and gum and causing discomfort, as well as potentially more severe periodontal disease.

DESCRIPTION OF THE PRIOR ART

Various types of devices are known in the field of orthodontics and periodontics for measuring interdental spacing and the depth of periodontal cavities. Gauge plates having a variety of thicknesses have long been used for insertion in interdental spaces, in order to measure the interproximal distance between adjacent teeth. These gauge plates, commonly known as dental contact gauges, are usually constructed of stainless steel and are provided with a grip portion which may be color-coded according to the thickness of the plate. Since the average interproximal distance between teeth is on the order of about 70-92 microns in the case of young men and women, the three sizes of dental contact gauges normally used are 50 microns, 110 microns and 150 microns in thickness. In diagnosis, the gauge plates are inserted into the interdentium in order of plate thickness, from the thinner gauge plate to the thicker one, until the succeeding gauge plate cannot be inserted therein. The dentist then estimates the interproximal distance under investigation according to data printed in a table provided with the instruments. U.S. Pat. No. 4,664,627, dated May 12, 1987, to Ikuo Kyotani, details a "Dental Contact Gauge" which is used for the examination of proximal spacing between adjacent teeth. The gauge is characterized by a gauge plate having a constant thickness and formed of a shape-memory alloy to facilitate conforming the gauge approximately to the contour of the adjacent teeth. The gauge is subsequently restored to its original shape at a temperature of at least 40 degrees Centigrade.

Tools used to probe the depth of tooth cavities and for other purposes, such as determining the depth of periodontal cavities in the practice of dentistry, are also well known in the art. An early dental tool for this purpose is detailed in U.S. Pat. No. 1,501,170, dated July 15, 1924, to F. W. Korb. The Korb measuring tool includes an elongated sleeve, one end of which is provided with an annular, radial rib shaped in the form of a collar and carried by a shell or guard member which is securely arranged over the sleeve end. The shell or guard extends over the sleeve a distance sufficient to entirely cover slits provided in the sleeve, in order to prevent accidental injury to the operator by a probe which is extended through one of the slits. The shell is provided with a pair of oppositely-disposed apertures, through which an instrument may be inserted to increase the tension in the gripping jaw. The rib or collar serves as a finger-piece for the user while adjusting the instrument. The forward end of the sleeve is snugly fitted within the inner end of a nipple which is tapered and curved to a comparatively small end adapted to rest upon a tooth at the entrance of a cavity, the depth of which is to be measured. In use, the end of the probe is inserted to the bottom of the cavity in the tooth and the operator then moves the sleeve forward until the tapered end contacts the tooth at the entrance to the cavity. The tool is then removed from the patient's mouth and the projecting portion of the probe is measured by a scale or rule to accurately determine the depth of the cavity in the tooth. A "Remote-Recording Periodontal Depth Probe" is detailed in U.S. Pat. No. 3,943,914, dated Mar. 16, 1976. The apparatus includes a protruding, removably attached, cylindrical probe tip which is partially ensheathed by a slidable tubular sleeve that is electrically connected by means of a transducer within the probe body to a remote recording device. Translational movement of the slidable tubular sleeve, which partially sheaths the probe tip, varies an electrical signal between the probe and the remote recording device according to the length of probe tip exposed. An operator-controlled foot switch is connected between the probe and the remote recording device, which arrangement allows the operator to insert the probe tip into the gingival sulcus, or periodontal cavity, and to adjust the slidable sleeve until it touches the margin of the gingiva before activating the remote recording device. When activated, the recorder produces a record of the electrical signal which corresponds to the length of the exposed probe tip and this record is representative of the depth of the periodontal cavity at the measured location. A periodontal probe is detailed in U.S. Pat. No. 4,364,730, dated Dec. 21, 1982, to Per A. T. Axelsson. The probe is characterized by a handle portion and a pin member rotatably mounted on the handle portion about an axis of rotation. The pin member further includes a free end portion which is straight and flat and lies to one side of and in the same plane as the axis of rotation. The spacing between the free end portion and the axis is either constant or decreases in a direction toward the free end of the free end portion. U.S. Pat. No. 4,677,756, dated July 7, 1987, to Louis A. Simon, et al, details "Measuring Instruments for Measuring the Depth of Cavities". In a preferred embodiment a probe device includes a probe element and a sheath, the probe element being slidable within the sheath and protruding therefrom in variable length. Further included is a means for producing a depth signal representing the amount of protrusion of the probe element from the sheath, means for monitoring the rate of change of the depth signal and means for recording and/or displaying a value which is presentative of the depth signal when the rate of change of the depth signal reaches a predetermined value. Other measuring devices used in the practice of dentistry are the "Two-Directional Measuring Devices" detailed in U.S. Pat. No. 4,473,952, dated Oct. 2, 1984, to Renato Mariani and U.S. Pat. No. 4,624,639, dated Nov. 25, 1986, to Brian W. Wong.

It is an object of this invention to provide a new and improved dental space and periodontal cavity measuring instrument for measuring interdental spaces and periodontal cavities in the upper and lower dental arches.

Another object of the invention is to provide a combined dental space and periodontal cavity measuring instrument which is characterized by a quantifiable gauge adapted to measure interdental spaces and periodontal cavities that are either mechanically created or naturally occurring and provided with at least one striation or groove on at least one end for tucking ligatures.

Still another object of this invention is to provide a dental space and periodontal cavity measuring instrument which is characterized by a handle and at least one set of graduated cylinders extending from the handle for insertion between adjacent teeth or in periodontal cavities adjacent to teeth in the dental arches to determine the size of the interdental spaces and the depth of the periodontal cavities with a high degree of accuracy.

Still another object of the invention is to provide a dental space and periodontal cavity measuring instrument which includes a handle and at least one elongated, calibrated and/or graduated tip extending from the handle, which graduated tip may either be straight or angulated for insertion in spaces between the teeth and into periodontal cavities adjacent to the teeth, to determine the width of such spaces and the depth of the periodontal cavities and facilitate accurate orthodontic and periodontic treatment.

Yet another object of the invention is to provide a combined dental space and periodontal cavity measuring instrument which includes a handle, a first elongated, calibrated member of selected length characterized by a first set of graduated cylinders extending from one end of the handle in angulated relationship and terminated by a graduated tip and a second elongated, calibrated member of selected length defined by a second set of graduated cylinders extending from the opposite end of the handle and a graduated tip extending from the opposite end of the handle in angulated relationship, wherein the graduated cylinders may be inserted in interdental spaces and the graduated tips into periodontal cavities, respectively, in the upper and lower dental arches to determine the magnitude of the interdental spaces and the depth of the periodontal cavities for orthodontic and periodontic treatment.

SUMMARY OF THE INVENTION

These and other objects of the invention are provided in a new and improved dental space and periodontal cavity measuring instrument which is characterized by an elongated handle having a first set of calibrated and graduated, angulated cylinders extending from one end thereof and a second set of calibrated and graduated, angulated cylinders extending from the opposite end of the handle, which cylinders are angulated at a selected point, wherein at least one of the distal cylinders are provided with waffled, ligature-engaging striations on the end thereof and appropriate indicia are provided on the handle for identifying the diameter of the intermediate cylinders, such that the intermediate cylinders and distal cylinders can be selectively inserted in interdental spaces and the distal cylinders into periodontal cavities in the upper and lower dental arches to determine the width of the interdental spaces and the depth of the periodontal cavities, respectively, and facilitate accurate orthodontic and periodontic treatment.

BRIEF DESCRIPTION OF THE DRAWING

The invention will be better understood by reference to the accompanying drawing, wherein:

FIG. 1 is a perspective view of a preferred embodiment of the dental space and periodontal cavity measuring instrument of this invention;

FIG. 2 is a sectional view of a tooth and underlying bone structure and the dental space and periodontic cavity measuring instrument illustrated in FIG. 1, with the graduated distal cylinder end portion inserted in a typical periodontal cavity;

FIG. 3 is an enlarged view, partially in section, of the dental space and periodontal cavity measuring instrument illustrated in FIG. 1, more particularly illustrating size indicia provided on the instrument handle;

FIG. 4 is a side view, partially in section, of an alternative handle configuration for the dental space and periodontal cavity measuring instrument illustrated in FIG. 1;

FIG. 5 is a side view, partially in section, of yet another alternative handle configuration of the dental space and periodontal cavity measuring instrument illustrated in FIG. 1;

FIG. 6 is an end view of the handle embodiment of the dental space and periodontal cavity measuring instrument illustrated in FIG. 4;

FIG. 7 is an end view of the handle embodiment of the dental space and periodontal cavity measuring instrument illustrated in FIG. 5;

FIG. 8 is a side view, partially in section, of an alternative preferred embodiment of the dental space and periodontal cavity measuring instrument of this invention; and FIG. 9 is an end view of the distal angulated cylinder end portion, more particularly illustrating waffled striations provided in the end portion.

DESCRIPTION OF THE PREFERRED EMBODIMENTS

Referring initially to FIGS. 1 and 3 of the drawing, in a preferred embodiment the dental space and periodontal cavity measuring instrument of this invention is generally indicated by reference numeral 1. The dental space and periodontal cavity measuring instrument 1 includes a round handle 2, provided with a handle taper 3 at each end, which handle taper 3 terminates at a taper margin 4. A graduated angulated tip 5 projects from each end of the round handle 2 and in a first preferred embodiment is defined by a pair of calibrated proximal angulated cylinders 6, which extend from the round handle 2 at the corresponding taper margin 4, two graduated calibrated intermediate cylinders 8, projecting respectively from the proximal angulated cylinders 6 in end-to-end relationship at the respective cylinder shoulders 10 and a calibrated distal angulated cylinder 7, which extends from the second intermediate cylinder 8 and terminates the extending end of the calibrated angulated tips 5, respectively. The proximal angulated cylinders 6, intermediate angulated cylinders 8 and distal angulated cylinders 7 are graduated in decreasing, graduated, calibrated diameter at each of the cylinder shoulders 10, which define cylinder junctions. The term "calibrated" is used to denote construction of each cylinder in a selected diameter for measuring interdental spacing. A cylinder bend 9 is provided in the first extending intermediate angulated cylinder 8 in one of the graduated angulated tips 5, to facilitate accessing interdental spaces which are located centrally and in the rear of the oral cavity, as described in my copending U.S. patent application Ser. No. 07/358,597, filed May 30, 1989. The distal angulated cylinders 7 may each be alternatively constructed to project directly from the first one of the intermediate angulated cylinders 8 or directly from the proximal angulated cylinders 6, respectively, under circumstances where the intermediate angulated cylinders 8 are omitted. Furthermore, the bend 9 may be provided in the distal angulated cylinders 7, as illustrated in the opposite one of the graduated angulated tips 5. Each distal angulated cylinder 7 terminates in a segment end 15, as illustrated.

Referring now to FIG. 8, the distal angulated cylinder 7 is defined by an unmarked cylinder segment 12 of uniform diameter, extending from the round handle 2 at the taper margin 4 of the handle taper 3, and a measuring cylinder segment 13, which extends from the unmarked cylinder segment 12 at a cylinder bend 9. Multiple, spaced cylinder marks 14 are provided on the measuring cylinder segment 13 and these cylinder marks 14 extend from the cylinder bend 9 to the segment end 15.

Referring again to FIGS. 1 and 3, it will be appreciated that either or both of the distal angulated cylinders 7 may be alternatively constructed to project directly from the second one of the intermediate angulated cylinders 8 in straight relationship, in the plane of the round handle 2, wherein the bend 9 is eliminated in either one or both of the intermediate angulated cylinders 8 and the distal angulated cylinders 7.

As further illustrated in FIG. 3, cylinder indicia 19 is provided on the handle 2 and the corresponding indicia arrows 22 indicate that the angulated cylinder indicia 19 is appropriate for designating the relative sizes of the proximal angulated cylinders 6, intermediate angulated cylinders 8 and the distal angulated cylinders 7, respectively, which define the calibrated angulated tip 5, on each end of the round handle 2, respectively.

Referring now to FIGS. 5 and 7, in another preferred embodiment of the invention the dental space measuring instrument 1 is characterized by a hexagonal handle 17, having five flat handle facets 18 and a flat indicia base 21, the latter of which receives the indicia arrow 22 and the cylinder indicia 19. Otherwise, the calibrated angulated tip or tips 5 of the dental space measuring instrument 1 are identical to the configuration illustrated in FIGS. 1-4.

As further illustrated in FIGS. 4 and 6, a knurled surface 23 may be provided in the round handle 2 and the indicia base 21 may be elevated from or coextensive with the knurled surface 23, in order to facilitate stamping or otherwise providing the angulated cylinder indicia 19 and the indicia arrow 22 thereon.

Referring now to FIGS. 1 and 2 of the drawing, a tooth 24, having a crown 25 and roots 26 is illustrated, with the distal angulated cylinder 7 of the angulated tip 5 extending into a periodontal cavity 28, located between the root 26 and the underlying bone 27, for measurement purposes. Since the tooth 24, typically a second premolar or a first premolar, may be located near the rear of the oral cavity, the cylinder bend 9, illustrated in FIG. 1, serves to facilitate easy manipulation of the distal angulated cylinder 7 into the periodontal cavity 28 to accurately determine the depth of the periodontal cavity 28. In this case, the depth of the periodontal cavity 28 is about 2 millimeters, as indicated by the cylinder marks 14.

As illustrated in FIG. 9 of the drawing, in yet another preferred embodiment of the invention the segment ends 15 of the elongated distal angulated cylinders 7 are flat or slightly rounded and provided with multiple striations 16, inscribed thereon in a waffled pattern, for engaging ligatures (not illustrated) used for securing braces, and tucking the ends of the ligatures, in orthodontic practice.

It will be appreciated by those skilled in the art that the dental space and periodontal cavity measuring instrument of this invention is characterized by a highly versatile, easily manipulated and efficient, calibrated tool for measuring both the interdental spaces and periodontal cavities located in both the upper and lower dental arches. It is understood that while the dental space and periodontal measuring instrument 1 illustrated in the drawing is characterized by a pair of angulated tips 5, each having four calibrated, graduated cylinders, the number of calibrated, graduated cylinders, as well as the provision of one or two of the angulated tips 5, the cross-sectional configuration of the angulated tip(s) 5 and the location of the cylinder bend 9 in the angulated tip(s) 5, is a matter of discretion according to the desire of the user. For example, the cylinder bend 9 may be located close to the taper margin 4 or even in the distal angulated cylinder 7, as illustrated in FIGS. 1, 3 and 8, in order to better reach the molar, second premolar and first premolar, as well as other teeth, respectively. Furthermore, the size and number of cylinders in the angulated tip(s) 5 can be selected according to variation in the size, location and frequency of interdental spaces and periodontal cavities in children and adults, respectively. Moreover, while the length and diameter or size of the proximal angulated cylinders 6 and distal angulated cylinders 7 may be varied, in a most preferred embodiment, this length is about 5 mm. Typical, but non-exclusive cylinder diameter dimensions, or side measurements, in the case of instruments having non-circular cross-sections, are 0.50, 0.75, 1.0, 1.25 1.75, 2.0, 2.25 and 2.5 millimeters for the distal angulated cylinders 7, intermediate angulated cylinders 8 and proximal angulated cylinders 6, respectively, as indicated in the cylinder indicia 19, provided on the round handle 2, illustrated in FIG. 3, the knurled surface 23, illustrated in FIG. 4 and the indicia base 21, illustrated in FIG. 5. However, it will be appreciated that other diameter dimensions or side measurements which are indicated in any desired units may also be used, as deemed necessary. As heretofore described, the cross-sectional configuration of the round handle 2 can be altered to define the hexagonal handle 17 or a handle shaped in the configuration of any regular polygon, or in any other configuration, as desired. Moreover, it will be further recognized that while stainless steel is the preferred material of choice for the dental space and periodontal cavity measuring instrument 1 since it can be sterilized in an autoclave, other materials of construction can be utilized, including injection-molded plastics, fiberglass and like resilient materials, and even wood, wherein the dental space and periodontal cavity measuring instrument 1 is discarded after each use.

While the preferred embodiments of the invention have been described above, it will be recognized and understood that various modifications may be made therein and the appended claims are intended to cover all such modifications which may fall within the spirt and scope of the invention.

Having described my invention with the particularity set forth above, what is claimed is:

1. A dental space and periodontal cavity measuring instrument comprising handle means, a first calibrated, graduated portion projecting from one end of said handle means and an end portion extending from said first calibrated, graduated portion in angular relationship for insertion in the dental space and the periodontal cavity and ;measuring the width of the dental space and the depth of the periodontal cavity and at least one measuring mark provided on said end portion for indicating the depth of the periodontal cavity.

2. The dental space measuring instrument of claim 1 wherein said first calibrated, graduated portion and said end portion further comprises a first plurality of calibrated, graduated cylinders for insertion in the dental space, with the largest of said first plurality of calibrated, graduated cylinders extending from one end of said handle means and the last one of said first plurality of calibrated, graduated cylinders defining a first end portion for insertion in the periodontal cavity, said first end portion having at least one of said measuring mark for indicating the depth of the periodontal cavity.

3. The dental space measuring instrument of claim 1 wherein said first calibrated, graduated portion and said end portion further comprises:

(a) a first plurality of calibrated, graduated cylinders adapted for insertion in the dental space, with the largest of said first plurality of calibrated, graduated cylinders extending from one end of said handle means and the smallest one of said first plurality of graduated cylinders adapted for insertion in the periodontal cavity and further comprising a first plurality of measuring marks provided on said smallest one of said first plurality of calibrated, graduated cylinders for indicating the depth of the periodontal cavity; and (b) a second plurality of calibrated, graduated cylinders adapted for insertion in the dental space, with the largest of said second plurality of calibrated, graduated cylinders extending from the opposite end of said handle means and the smallest one of said second plurality of graduated cylinders adapted for insertion in the periodontal cavity and further comprising a second plurality of measuring marks provided on the smallest one of said second plurality of calibrated, graduated cylinders for indicating the depth of the periodontal cavity.

4. The dental space measuring instrument of claim 3 further comprising measuring indicia provided on said handle means for indicating the size of said first and second plurality of calibrated, graduated cylinders, respectively.

5. The dental space measuring instrument of claim 1 further comprising:

a second calibrated, graduated portion projecting from the opposite end of said handle means and a second end portion extending from said second calibrated, graduated portion in angular relationship, said second end portion further characterized by at least one measuring mark, and further comprising measuring indicia provided on said handle means for indicating the size of said first calibrated, graduated portion, said end portion and said second calibrated, graduated portion and said second end portion, respectively.

6. The dental space measuring instrument of claim 5 wherein:

(a) said first calibrated, graduated portion further comprises a first plurality of calibrated, graduated cylinders adapted for insertion in the dental space, with the largest of said first plurality of calibrated, graduated cylinders extending from said one end of said handle means and the smallest of said first plurality of calibrated, graduated cylinders defined by said end portion for indicating the depth of the periodontal cavity;

(b) said second calibrated, graduated portion further comprises a second plurality of calibrated, graduated cylinders adapted for insertion in the dental space, with the largest of said second plurality of calibrated, graduated cylinders extending from said opposite end of said handle means and the smallest of said second plurality of calibrated, graduated cylinders defined by said second end portion for indicating the depth of the periodontal cavity; and (c) said measuring indicia corresponds to the calibrated diameter of said first plurality of calibrated, graduated cylinders and said second plurality of calibrated, graduated cylinders, respectively.

7. An instrument for measuring interdental spacing and periodontal cavities, comprising an elongated handle, a first plurality of calibrated, graduated cylinders, with the largest one of said first plurality of calibrated, graduated cylinders extending from one end of said handle and the smallest one of said first plurality of calibrated, graduated cylinders defining a first end portion, at least one first measuring mark provided on said first end portion of said first plurality of calibrated, graduated cylinders, a second plurality of calibrated, graduated cylinders, with the largest one of said second plurality of calibrated, graduated cylinders extending from said opposite end of said handle and the smallest one of said second plurality of calibrated, graduated cylinders defining a second end portion of said second plurality of calibrated, graduated cylinders, whereby at least a portion of said first plurality of calibrated, graduated cylinders and said second plurality of calibrated, graduated cylinders are selectively inserted between adjacent teeth for measuring the interdental spacing and said first end portion and said second end portions are selectively inserted in the periodontal cavities for measuring the depth of the periodontal cavities.

8. The instrument of claim 7 wherein selected ones of said first plurality of calibrated, graduated cylinders and said second plurality of calibrated, graduated cylinders are angulated with respect to the longitudinal plane of said handle.

9. The instrument of claim 7 wherein said first plurality of calibrated, graduated cylinders and said second plurality of calibrated, graduated cylinders project substantially in the longitudinal plane of said handle.

10. The instrument of claim 7 wherein selected ones of said first plurality of calibrated, graduated cylinders are angulated with respect to the longitudinal plane of said handle and said second plurality of calibrated, graduated cylinders project from said opposite end of said handle substantially in the longitudinal plane of said handle.

11. The instrument of claim 7 further comprising first numerical indicia provided on said handle for indicating the diameter of said first calibrated plurality of calibrated, graduated cylinders and second numerical indicia provided on said handle for indicating the diameter of said second plurality of calibrated, graduated cylinders.

12. The instrument of claim 11 wherein selected ones of said first plurality of calibrated, graduated cylinders are angulated with respect to the longitudinal plane of said handle.

13. The instrument of claim 11 wherein second plurality of calibrated, graduated cylinders project from said opposite end of said handle substantially in the longitudinal plane of said handle.

14. The instrument of claim 11 wherein selected ones of said first plurality of calibrated, graduated cylinders are angulated with respect to the longitudinal plane of said handle and said second plurality of calibrated, graduated cylinders project from said opposite end of said handle substantially in the longitudinal plane of said handle.

15. The instrument of claim 11 further comprising arrow indicia provided on said handle for indicating which of said numerical indicia is applicable to said first plurality of calibrated, graduated cylinders and said second plurality of calibrated, graduated cylinders, respectively.

16. The instrument of claim 15 wherein selected ones of said first plurality of calibrated, graduated cylinders and said second plurality of calibrated, graduated cylinders are angulated with respect to the longitudinal plane of said handle.

* * * * *